(12) United States Patent
Gliner et al.

(10) Patent No.: US 11,596,324 B2
(45) Date of Patent: Mar. 7, 2023

(54) COMBINED ACTIVE CURRENT LOCATION (ACL) AND TISSUE PROXIMITY INDICATION (TPI) SYSTEM

(71) Applicant: Biosense Webster (Israel) Ltd., Yokneam (IL)

(72) Inventors: Vadim Gliner, Haifa (IL); Assaf Govari, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 1126 days.

(21) Appl. No.: 16/170,661

(22) Filed: Oct. 25, 2018

(65) Prior Publication Data

US 2020/0129089 A1 Apr. 30, 2020

(51) Int. Cl.
| | | |
|---|---|---|
| *A61B 5/00* | (2006.01) | |
| *A61B 18/14* | (2006.01) | |
| *A61B 5/283* | (2021.01) | |
| *A61B 5/06* | (2006.01) | |
| *A61B 5/0295* | (2006.01) | |
| *A61B 18/00* | (2006.01) | |

(52) U.S. Cl.
CPC ............ *A61B 5/063* (2013.01); *A61B 5/0295* (2013.01); *A61B 5/283* (2021.01); *A61B 5/6858* (2013.01); *A61B 18/1492* (2013.01); *A61B 2018/00351* (2013.01); *A61B 2018/00577* (2013.01); *A61B 2562/0209* (2013.01); *A61B 2562/0257* (2013.01)

(58) Field of Classification Search
CPC .......... A61B 5/25; A61B 5/283; A61B 5/027; A61B 5/063; A61B 5/0659; A61B 5/068; A61B 18/1492; A61B 2018/00351; A61B 2018/00577; A61B 2562/0257
See application file for complete search history.

(56) References Cited

U.S. PATENT DOCUMENTS

| | | |
|---|---|---|
| 5,499,981 A | 3/1996 | Kordis |
| 5,662,108 A | 9/1997 | Budd et al. |
| 5,792,070 A | 8/1998 | Kauphusman et al. |

(Continued)

FOREIGN PATENT DOCUMENTS

| | | |
|---|---|---|
| EP | 1 743 573 A2 | 1/2007 |
| EP | 1897587 A2 | 3/2008 |

(Continued)

OTHER PUBLICATIONS

U.S. Appl. No. 15/857,101, filed Dec. 28, 2017.

(Continued)

*Primary Examiner* — Eun Hwa Kim
(74) *Attorney, Agent, or Firm* — Scully, Scott, Murphy & Presser, PC

(57) ABSTRACT

A method includes transmitting electrical signals between one or more pairs of body-surface electrodes attached to a body of a patient. Electrical potentials resulting from the transmitted electrical signals are acquired by an outer-facing electrode and an inner-facing electrode of a medical probe inserted in an organ of the patient. A proximity of the medical probe to surface tissue of the organ is estimated based on the electrical potentials acquired by the outer-facing electrode. A position of the medical probe within the organ is estimated based on the electrical potentials acquired by the inner-facing electrode.

16 Claims, 2 Drawing Sheets

(56) References Cited

U.S. PATENT DOCUMENTS

| | | |
|---|---|---|
| 5,983,126 A | 11/1999 | Wittkampf |
| 6,050,267 A | 4/2000 | Nardella et al. |
| 6,391,024 B1 | 5/2002 | Sun et al. |
| 6,405,067 B1 | 6/2002 | Mest et al. |
| 7,756,576 B2 | 7/2010 | Levin |
| 7,848,787 B2 | 12/2010 | Osadchy |
| 7,869,865 B2 | 1/2011 | Govari et al. |
| 8,456,182 B2 | 6/2013 | Bar-Tal et al. |
| 9,655,677 B2 | 5/2017 | Salahieh et al. |
| 2002/0029062 A1 | 3/2002 | Satake |
| 2002/0151807 A1 | 10/2002 | Goldin |
| 2005/0288719 A1 | 12/2005 | Zhang et al. |
| 2006/0173251 A1 | 8/2006 | Govari et al. |
| 2009/0099618 A1 | 4/2009 | Rousso et al. |
| 2009/0275827 A1 | 11/2009 | Aiken et al. |
| 2012/0130267 A1 | 5/2012 | Harlev et al. |
| 2013/0109906 A1 | 5/2013 | Valoir |
| 2013/0150693 A1 | 6/2013 | D'Angelo et al. |
| 2014/0121641 A1 | 5/2014 | Fischell et al. |
| 2015/0351652 A1 | 12/2015 | Marecki |
| 2015/0366481 A1* | 12/2015 | Voth ................ A61B 5/316 600/523 |
| 2015/0366508 A1 | 12/2015 | Chou et al. |
| 2016/0287137 A1 | 10/2016 | Condie et al. |
| 2016/0317093 A1* | 11/2016 | Berenfeld ............ A61B 5/068 |
| 2017/0042615 A1 | 2/2017 | Salahieh et al. |
| 2017/0172442 A1 | 6/2017 | Govari |
| 2018/0199976 A1 | 7/2018 | Fischer |

FOREIGN PATENT DOCUMENTS

| | | |
|---|---|---|
| EP | 3115011 A1 | 1/2017 |
| WO | WO 2011/005165 A1 | 1/2011 |
| WO | 2016/183285 A1 | 11/2016 |

OTHER PUBLICATIONS

U.S. Appl. No. 15/966,514, filed Apr. 30, 2018.
U.S. Appl. No. 15/991,291, filed May 29, 2018.
Extended Supplementary European Search Report dated Dec. 3, 2019 in European Patent Application No. 19 20 5093.8.
Office Action dated Oct. 6, 2021 issued in the EPO from related European Patent Application No. 19 205 093.8.

* cited by examiner

COMBINED ACTIVE CURRENT LOCATION (ACL) AND TISSUE PROXIMITY INDICATION (TPI) SYSTEM

CROSS-REFERENCE TO RELATED APPLICATIONS

This application is related to a U.S. Patent entitled "ELECTRODES ON DOUBLE-SIDED PRINTED CIRCUIT BOARD (PCB) TO CANCEL FAR-FIELD SIGNAL,", U.S. patent Ser. No. 11/452,484 B2, granted on Sep. 27, 2022 and to a provisional U.S. Patent Application entitled "BALLOON CATHETER WITH DIAGNOSTIC ELECTRODES, FAR FIELD DETECTION ELECTRODES, AND GUIDEWIRE,", Application No. 62/750,461 filed on Oct. 25, 2018, whose disclosures are incorporated herein by reference.

FIELD OF THE INVENTION

The present invention relates generally to systems and methods for tracking medical probes within a patient's body, and specifically to impedance based cardiac position tracking systems and methods.

BACKGROUND OF THE INVENTION

Various methods for tracking a catheter position within a patient's heart were proposed. For example, U.S. Patent Application Publication 2012/0130267 described methods and systems for the determination and representation of a chamber anatomy using a basket catheter. In some embodiments, a local surface is generated for a particular catheter location. The system detects and marks regions of the local parameterized surface that are valid. Valid regions of the local surface are region(s) that are expected to lie on the true chamber boundary. The catheter is then moved to another location and the process of construction of local anatomy and detection of valid patches is repeated.

As another example, U.S. Pat. No. 5,983,126 describes a system and method for catheter location mapping, and related procedures. Three substantially orthogonal alternating signals are applied through the patient, directed substantially toward the area of interest to be mapped, such as patient's heart. A catheter is equipped with at least a measuring electrode, which for cardiac procedures is positioned at various locations either against the patient's heart wall, or within a coronary vein or artery. A voltage is sensed between the catheter tip and a reference electrode, preferably a surface electrode on the patient, which voltage signal has components corresponding to the three orthogonally applied current signals. Three processing channels are used to separate out the three components as x, y and z signals, from which calculations are made for determination of the three-dimensional location of the catheter tip within the body.

U.S. Patent Application Publication 2016/0287137 describes a method and system for assessing electrode-tissue contact before the delivery of ablation energy. The method may generally include determining a difference between a maximum impedance magnitude at a low frequency for a given electrode and an absolute minimum impedance magnitude at the low frequency across all electrodes, determining a difference between a maximum impedance magnitude at a high frequency for a given electrode and an absolute minimum impedance magnitude at the high frequency across all electrodes, and determining a difference between a maximum impedance phase at the high frequency for a given electrode and an absolute minimum impedance phase at the high frequency across all electrodes. These differences may be correlated to one another using a linear model, the results of which determining whether the given electrode is in contact or not in contact with tissue.

SUMMARY OF THE INVENTION

An embodiment of the present invention provides a method including transmitting electrical signals between one or more pairs of body-surface electrodes attached to a body of a patient. Electrical potentials resulting from the transmitted electrical signals are acquired by an outer-facing electrode and an inner-facing electrode of a medical probe inserted in an organ of the patient. A proximity of the medical probe to surface tissue of the organ is estimated based on the electrical potentials acquired by the outer-facing electrode. A position of the medical probe within the organ is estimated based on the electrical potentials acquired by the inner-facing electrode.

In some embodiments, estimating the position of the probe includes calculating a position of the outer-facing electrode based on (i) the estimated position of the inner-facing electrode, and (ii) a known geometrical relation between the outer-facing electrode and the inner-facing electrode in the probe.

In some embodiments, transmitting the electrical signals includes transmitting a superposition of a first signal having a first frequency, and a second signal having a second frequency higher than the first frequency.

In an embodiment, estimating the tissue proximity includes calculating a ratio between a first impedance and a second impedance that were derived from the acquired potentials at the first-frequency and the second-frequency, respectively, and calculating the tissue proximity based on the ratio.

In another embodiment, estimating the position of the probe includes calculating impedances derived from the potentials acquired by the inner-facing electrode at the first-frequency, and calculating the position of the probe based on the impedances.

In some embodiments, the outer-facing electrode and the inner-facing electrode are disposed directly opposite each other.

In some embodiments, acquiring the electrical potentials includes acquiring electrical potentials propagating in blood.

In an embodiment, acquiring the electrical potentials includes acquiring the electrical potentials propagating in tissue in contact with the outer-facing electrode. There is additionally provided, in accordance with an embodiment of the present invention, a system including one or more pairs of body-surface electrodes and a processor. The one or more pairs of body-surface electrodes are configured to be attached to a body of a patient and to transmit electrical signals into the body. The processor is configured to receive signals indicative of electrical potentials that are acquired by an outer-facing electrode and an inner-facing electrode of a medical probe inserted in an organ of the patient, resulting from the transmitted electrical signals. The processor is further configured to estimate a proximity of the medical probe to surface tissue of the organ based on the signals indicative of the electrical potentials acquired by the outer-facing electrode, and to estimate a position of the medical probe within the organ based on the signals indicative of the electrical potentials acquired by the inner-facing electrode.

The present invention will be more fully understood from the following detailed description of the embodiments thereof, taken together with the drawings in which:

DETAILED DESCRIPTION OF EMBODIMENTS

Overview

Figure 1:
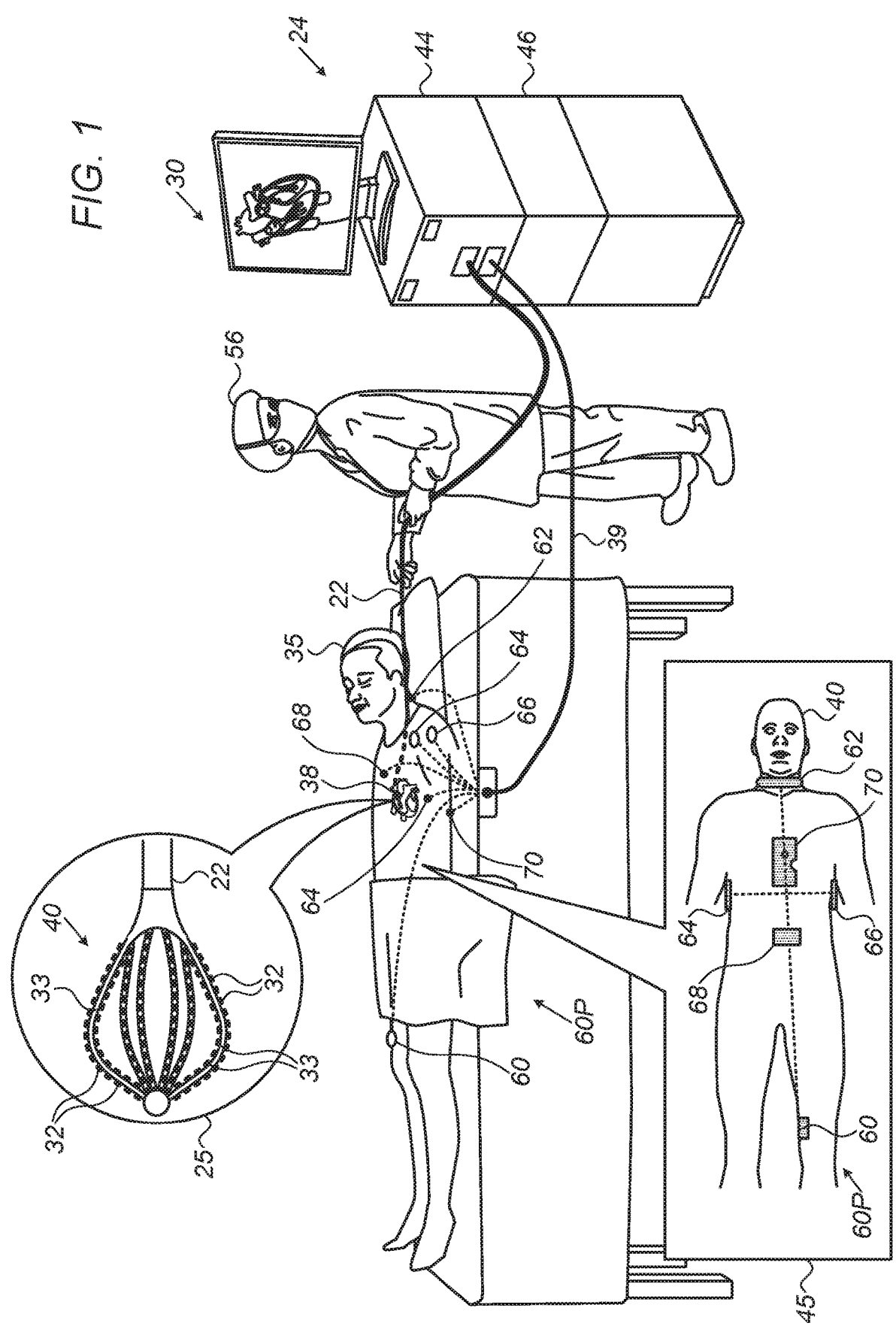
FIG. 1 is a schematic, pictorial illustration of a catheter-based electroanatomical (EA) mapping system, in accordance with an embodiment of the present invention.

Embodiments of the present invention that are described herein provide methods and systems for tracking the position of a catheter inside a cavity of an organ, such as a heart, of a patient and, at a same time, indicating cavity tissue proximity to the catheter. The disclosed methods and systems can be applied to various types of catheters fitted with two kinds of distal electrodes, the first being an "outer-facing" electrode that can contact cardiac tissue, and the second being an "inner-facing" electrode that cannot come in physical contact with tissue, but only with cardiac blood. The two types of distal electrodes are electrically isolated from each other. Typically, but not necessarily, both such distal electrodes are placed on a same spine of a catheter, directly opposite each other, as described below.

In some embodiments, a processor of an electrical catheter-based electroanatomical (EA) mapping system estimates proximity of the medical probe (e.g., of an outer-facing electrode of the probe) to surface tissue of the organ based on electrophysiological (EP) signals acquired using the outer-facing electrode. Based on EP signals acquired using an inner-facing electrode, the processor derives the position of the corresponding outer-facing electrode. Typically, the processor derives the position of the outer-facing electrode from the position of the corresponding inner-facing electrode using the known geometry of the probe. The simultaneously acquired position and tissue proximity indications enables the EA system to accurately and rapidly map a cavity of the organ, such as a cardiac chamber of the heart, using only electrical signals.

To generate the signals, in some embodiments, the disclosed catheter-based EA mapping system comprises three approximately mutually orthogonal pairs of body-surface electrodes. A position tracking system having such three largely mutually orthogonal pairs of body-surface electrodes is described, for example, in U.S. patent application Ser. No. 15/966,514, filed Apr. 30, 2018, entitled "Improved Active Voltage Location (AVL) Resolution," which is assigned to the assignee of the present patent application and whose disclosure is incorporated herein by reference.

In an embodiment, the EA system applies a superposition of two modulated voltages between each pair of body-surface electrodes. The first voltage is modulated at a first frequency, and the second voltage is modulated at a second frequency higher than the first frequency. The first modulation frequency is named hereinafter "low-frequency" and the second modulation frequency is named hereinafter "high-frequency." The respectively induced high- and low-frequency potentials in the heart are acquired by both the outer-facing electrodes and the inner-facing electrodes of the catheter, and transmitted to readout circuitry and a processor of the EA system. Typically, the low-frequency is in the range of several kHz, and the high-frequency is in the range of a few tens of kHz.

Based on electrical impedances calculated from the high- and low-frequency potentials acquired by an outer-facing electrode, the processor provides a tissue proximity indication (TPI) of the corresponding outer-facing electrode. In an embodiment, TPI is derived based on a calculated ratio between the low-frequency and the high-frequency impedances. Typically, this ratio is approximately unity in blood, but increases substantially (e.g., by a factor of up to three in cardiac tissue) when the outer-facing electrode contacts tissue.

An example method for determining whether or not an electrode of a catheter is in physical contact with tissue of an organ, which compares low- and high-frequency measured impedances between a catheter electrode and one or more body-surface electrodes, is described in U.S. patent application Ser. No. 15/991,291, filed May 29, 2018, entitled "Touch Detection Based on Frequency Response of Tissue," which is assigned to the assignee of the present patent application and whose disclosure is incorporated herein by reference.

Based on electrical impedances calculated from the potentials measured by an inner-facing electrode, the processor calculates (i.e., estimates) a position of the inner-facing electrode (i.e., using ACL or AVL). In some embodiments, a basket catheter, comprising an expandable frame comprising spines, is used for EA mapping of a cavity of the heart. Outer-facing and inner-facing electrodes are disposed over the spines and are operated by an EA mapping system for the EA mapping, combining ACL and TPI, as described below.

Typically, the Processor is programmed in software containing a particular algorithm that enables the processor to conduct each of the processor related steps and functions outlined above.

The disclosed methods, which combine ACL and TPI using inner-facing and outer-facing electrodes, respectively, may provide rapid and accurate EA mapping of a cavity of the heart, using a simple electrical set-up. Thus, the disclosed techniques may ease and therefore also increase availability of minimally invasive diagnostic and therapeutic solutions.

System Description

FIG. 1 is a schematic, pictorial illustration of a catheter-based electroanatomical mapping system 30, in accordance with an embodiment of the present invention. System 30 combines ACL and TPI for electroanatomical mapping using of a basket catheter 40, which is fitted at a distal end of a shaft 22, as seen in inset 25.

Catheter 40 is inserted by a physician 56 into an internal body cavity, such as a chamber of a heart 38 of a patient 35. Catheter 40 comprises one or more outer-facing electrodes 32, and inner-facing electrodes 33, as further seen in inset 25. Electrodes 32 and 33 are electrically isolated from each other and therefore separately connected by wires through shaft 22 to a driver circuitry 44 connected to a processor 46 included in a console 24. Driver circuitry 44 drives electrodes 32 and 33, as instructed by processor 46. For clarity and simplicity, embodiments using a single outer-facing electrode 32, and a single inner-facing electrode 33 directly opposite outer-facing electrode 32 are described hereinafter.

Processor 46 typically comprises a general-purpose computer, with a suitable front end, interface circuits for transmitting and receiving signals from three approximately mutually orthogonal pairs surface-electrodes 60P, and appropriate signal processing circuits. This is accomplished by using a driver circuitry 44 connected by wires through cable 39 to six surface-electrodes attached to the skin of the patient, which are named hereinafter patches 60, 62, 64, 66, 68, and 70, or collectively named hereinafter "patches 60P."

As seen in inset 45, patches 60P are distributed on the body of patient 35. By way of example, patch 60 is located on a thigh, patch 62 is located on the nape of the neck, patches 64 and 66 are located on both sides of the chest (under the arms), while patches 68 and 70 are located adjacent to a heart 38 on the chest and on the back, respectively.

In an embodiment, a superposition of voltages, modulated at a low-frequency and at a high-frequency, are applied between each of the three pairs of orthogonal surface electrodes 60P. The first, relatively high frequency, is in the 12-100 kHz range, and the second, relatively low frequency, is in the 1-5 kHz range.

Altogether, there are typically six distinct signals: two frequencies for each of the three pairs of body-surface electrodes. Electrodes 32 and 33 therefore measure six resulting voltages induced at heart 38, which are typically converted to impedances (i.e., using the aforementioned AVL or ACL methods).

ACL or AVL acquisition at a low frequency is more accurate than those made in a high frequency. However, the low-frequency position signal is sensitive to tissue contact. Thus, to obtain an exact position of the catheter when an outer-facing electrode is in physical contact with tissue, a low-frequency position-signal is acquired by the directly opposite inner-facing electrode 33.

Location-measuring system 30 may be used in other body cavities. Other probes can be used, which have a confined volume that can include inner-facing electrodes. Examples of catheter geometries having a similar confined volume are the PENTARY® and the LASSO®, made both by Biosense-Webster.

Typically, system 30 includes other elements, which are not shown in the figures for the sake of simplicity, and which are referred to, as necessary, in the following description. For example, system 30 may include an ECG monitor, coupled to receive signals from one or more body surface ECG electrodes, so as to provide an ECG synchronization signal to console 24. As another example, system 30 may comprise one or more additional catheters, such as an ablation catheter and/or an additional mapping-catheter. Thus, the configuration of FIG. 1 is an example configuration, which is chosen purely for the sake of conceptual clarity. In alternative embodiments, any other suitable configuration can also be used.

Another method for position sensing of an electrode of a catheter using body-surface electrodes is Active Current Location (ACL), which is implemented in various medical applications, for example, in the CARTO™ system, produced by Biosense-Webster Inc. (Irvine, Calif.) and described in detail in U.S. Pat. Nos. 7,756,576, 7,869,865, 7,848,787, and 8,456,182 whose disclosures are all incorporated herein by reference.

Processor 46 typically comprises a general-purpose processor, which is programmed in software to carry out the functions described herein. The software may be downloaded to the processor in electronic form, over a network, for example, or it may, alternatively or additionally, be provided and/or stored on tangible media, such as magnetic, optical, or electronic memory.

In particular, processor 46 runs a dedicated algorithm that enables processor 46 to perform the disclosed steps, comprising calculations of the locations and respective proximities.

Figure 2:
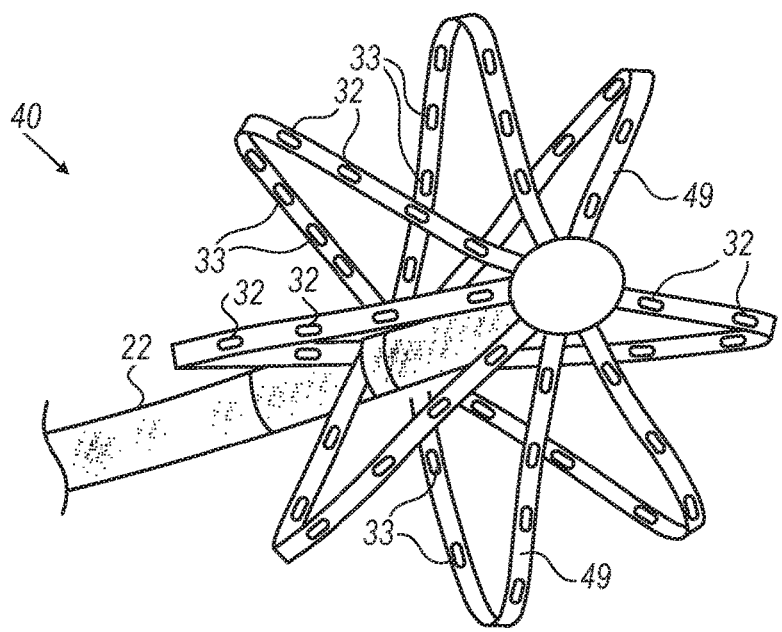
FIG. 2 is schematic, pictorial illustration of a basket catheter used by the EA system of FIG. 1, in accordance with an embodiment of the present invention.

Combined Active Current Location (ACL) and
Tissue Proximity Indication (TPI) System FIG. 2 is schematic, pictorial illustration of a basket catheter used by the EA system of FIG. 1, in accordance with an embodiment of the present invention. As seen, catheter 40, which is coupled to a distal end of shaft 22, comprises a plurality of expandable spines 49.

Each spine 49 carries, on its exterior, multiple outer-facing electrodes 32. Thus, when catheter 40 is positioned inside a cavity of heart 38 to acquire diagnostic EP signals, some of the outer-facing electrodes 32 repeatedly contact tissue. Respective multiple inner-facing electrodes 33 are carried by spines 49 directly opposite outer-facing electrodes 32, and can be distinguished as facing an internal volume defined by a surface of revolution about shaft 22 defined by spines 49. Each inner-facing electrode 33, opposite a respective outer-facing electrode 32, comes in contact only with blood.

As indicated above, each of both outer-facing electrode 32 and the directly opposite inner-facing electrode 33 acquire a superposition of high-frequency and low-frequency electrical signals. In some embodiments, based on electrical impedances calculated from the high- and low-frequency signals acquired by an outer-facing electrode 32, the processor provides a tissue proximity indication (TPI) of the catheter. Based on electrical impedances calculated from the low-frequency signals acquired by an inner-facing electrode 33, the processor calculates the position of the catheter at a same time that TPI was indicated (i.e., using aforementioned ACL or AVL).

The illustration shown in FIG. 2 is chosen purely for the sake of conceptual clarity. FIG. 2 shows only parts relevant to embodiments of the present invention. For example, other possible elements of catheter 40, such as ablation electrodes and temperature sensors are omitted for clarity.

Figure 3:
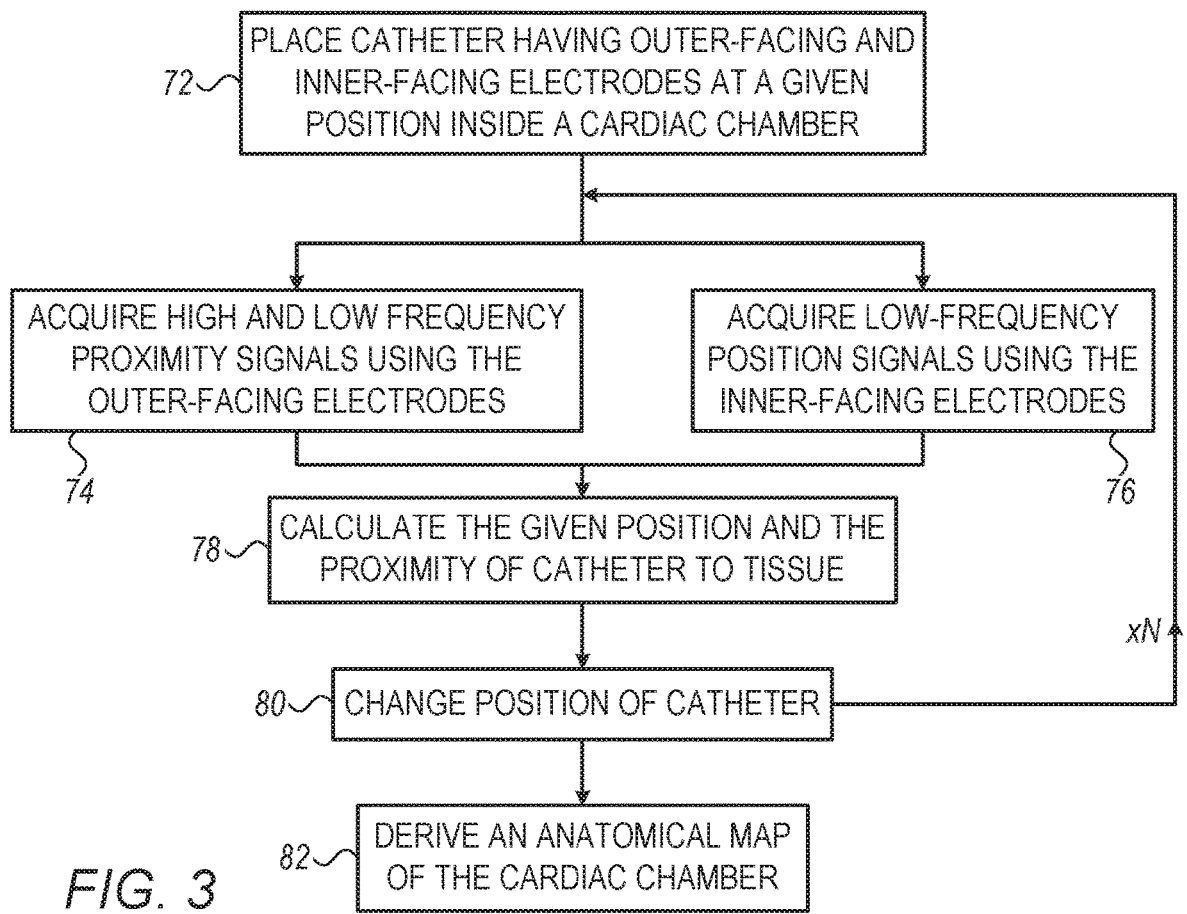
FIG. 3 is a flow chart that schematically illustrates a method for EA mapping by combining active current location (ACL) and tissue proximity indication (TPI), in accordance with an embodiment of the present invention.

FIG. 3 is a flow chart that schematically illustrates a method for EA mapping by combining active current location (ACL) and tissue proximity indication (TPI), in accordance with an embodiment of the present invention. The process begins with physician 56 placing catheter 40 at a given position inside a cavity of an organ, such as inside a cardiac chamber, at a catheter positioning step 72. Next, the EA mapping system 30, which transmits a superposition of modulated voltages between pairs of body-surface electrodes 60P, acquires substantially in parallel, proximity signals using outer-facing electrodes 32, at a proximity acquisition step 74, and position signals using inner-facing electrodes 33, at a position acquisition step 76. Based on an essentially simultaneous acquisition of proximity and position signals, processor 46 provides, using the dedicated algorithm, TPI and ACL of catheter 40 inside the cavity, at a location and proximity calculation step 78. As physician 56 repeatedly changes the position of catheter 40 inside the cavity (e.g., for N times), at a position change step 80, the process of steps 74-78 repeats itself. Based on the 2N TPI and ACL indications calculated by processor 46, processor 46 derives an anatomical map of the cavity (e.g., of the cardiac chamber), at an anatomical map derivation step 82.

The flow chart shown in FIG. 3 is chosen purely for the sake of conceptual clarity. For example, in alternative embodiments, at each position of catheter 40, system 30 further obtains an intra-cardiac electrocardiogram.

In an embodiment, based on electrical impedances calculated from the low-frequency measured signals, the processor calculates a position of the inner-facing electrodes (i.e., using ACL or AVL). The low frequency signals are used since, in general, low-frequency position signals are somewhat more accurate than high-frequency signal.

In an alternative embodiment, the high-frequency signal, which is also acquired by the outer-facing electrodes, is used as an extra position signal, for example, to remove any ambiguity in position that is measured using the inner-facing electrodes. The high-frequency signal can sometimes be used in this way, since it is largely insensitive to tissue contact. In another embodiment, TPI is established using the ratio of the low-frequency impedances measured with an outer-facing electrode and the opposite inner-facing electrode. The inner-facing electrode may be used since it in contact with blood only.

Although the embodiments described herein mainly address cardiac applications, the methods and systems described herein can also be used in other applications, such as in anatomical mapping of large blood vessels at different locations in the body.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A method, comprising:
   transmitting electrical signals between one or more pairs of body-surface electrodes attached to a body of a patient;
   acquiring, by an outer-facing electrode and an inner-facing electrode of a medical probe inserted in an organ of the patient, electrical potentials resulting from the transmitted electrical signals, the outer-facing electrode and the inner-facing electrodes being electrically isolated from each other;
   based on the electrical potentials acquired only by the outer-facing electrode, estimating a proximity of the outer-facing electrode to surface tissue of the organ;
   based on the electrical potentials acquired only by the inner-facing electrode, estimating a position of the inner facing electrode within the organ; and
   estimating a position of the outer-facing electrode within the organ based on the electrical potentials acquired by the inner facing electrode.

2. The method according to claim 1, wherein estimating a position of the medical probe within the organ comprises calculating the position of the outer-facing electrode within the organ based on (i) the estimated position of the inner-facing electrode, and (ii) a known geometrical relation between the outer-facing electrode and the inner-facing electrode in the medical probe.

3. The method according to claim 1, wherein transmitting the electrical signals comprises transmitting a superposition of a first signal having a first frequency, and a second signal having a second frequency higher than the first frequency.

4. The method according to claim 3, wherein estimating a proximity of the tissue to the medical probe comprises calculating a ratio between a first impedance and a second impedance derived from the acquired potentials resulting from the transmitted signals at the first-frequency and the second-frequency, respectively, and calculating the proximity of the tissue to the medical probe based on the ratio.

5. The method according to claim 3, wherein estimating the position of the medical probe comprises calculating impedances derived from the electrical potentials acquired by the inner-facing electrode resulting from the transmitted signals at the first-frequency, and calculating the position of the medical probe based on the impedances.

6. The method according to claim 1, wherein the outer-facing electrode and the inner-facing electrode are disposed directly opposite each other.

7. The method according to claim 1, wherein acquiring the electrical potentials comprises acquiring electrical potentials propagating in blood in contact with the inner-facing electrode.

8. The method according to claim 1, wherein acquiring the electrical potentials comprises acquiring the electrical potentials propagating in tissue in contact with the outer-facing electrode.

9. A system, comprising:
   one or more pairs of body-surface electrodes, which are configured to be attached to a body of a patient and to transmit electrical signals into the body; and
   a processor, which is configured to:
      receive signals indicative of electrical potentials that are acquired by an outer-facing electrode and an inner-facing electrode of a medical probe inserted in an organ of the patient, resulting from the transmitted electrical signals, the outer-facing electrode and the inner-facing electrodes being electrically isolated from each other;
      based on the signals indicative of the electrical potentials acquired only by the outer-facing electrode, estimate a proximity of the medical probe to surface tissue of the organ;
      based on the signals indicative of the electrical potentials acquired only by the inner-facing electrode, estimate a position of the inner-facing electrode within the organ; and
      estimating a position of the outer-facing electrode within the organ based on the electrical potentials acquired by the inner facing electrode.

10. The system according to claim 9, wherein the processor is configured to estimate a position of the medical probe within the organ by calculating the position of the outer-facing electrode within the organ based on (i) the estimated position of the inner-facing electrode, and (ii) a known geometrical relation between the outer-facing electrode and the inner-facing electrode in the probe.

11. The system according to claim 9, wherein the one or more pairs of body-surface electrodes are configured to transmit a superposition of a first signal having a first frequency, and a second signal having a second frequency higher than the first frequency.

12. The system according to claim 11, wherein the processor is configured to estimate a proximity of the tissue to the medical probe by calculating a ratio between a first impedance and a second impedance derived from the acquired potentials resulting from the transmitted signals at the first-frequency and the second-frequency, respectively, and calculating the proximity of the tissue to the medical probe based on the ratio.

13. The system according to claim 11, wherein the processor is configured to estimate the position of the medical probe by calculating impedances derived from the electric potentials acquired by the inner-facing electrode resulting from the transmitted signals at the first-frequency, and calculating the position of the medical probe based on the impedances.

14. The system according to claim 9, wherein the outer-facing electrode and the inner-facing electrode are disposed directly opposite each other.

15. The system according to claim 9, wherein the one or more pairs of body-surface electrodes are configured to receive electrical potentials propagating in blood in contact with the inner-facing electrode.

16. The system according to claim 9, wherein the one or more pairs of body-surface electrodes are configured to receive electrical potentials propagating in tissue in contact with the outer-facing electrode.

* * * * *